United States Patent [19]

Siegle et al.

[11] 4,027,037

[45] May 31, 1977

[54] N-SUBSTITUTED β-AMINOCROTONIC ACID ESTERS

[75] Inventors: Peter Siegle, Cologne; Klaus Sasse, Schildgen; Peter Rössler, Cologne, all of Germany

[73] Assignee: Bayer Aktiengesellschaft, Leverkusen, Germany

[22] Filed: Mar. 12, 1975

[21] Appl. No.: 557,698

[30] Foreign Application Priority Data

Mar. 26, 1974 Germany .......................... 2414456

[52] U.S. Cl. .................. 424/314; 260/239 BE; 260/239 BF; 260/247.2 B; 260/268 R; 260/293.88; 260/326.43; 260/340.5; 260/347.4; 260/468 G; 260/468 J; 260/470; 260/471 A; 260/479 S; 260/481 R; 260/482 R; 424/244; 424/2 48.52; 424/250; 424/267; 424/274; 424/282; 424/285; 424/299; 424/309; 424/248.55

[51] Int. Cl.² .............. C07C 101/28; A01N 9/20

[58] Field of Search ............... 260/482 R; 424/314

[56] References Cited

UNITED STATES PATENTS

| | | | |
|---|---|---|---|
| 2,578,788 | 12/1951 | Benneville | 260/482 R |
| 2,588,696 | 2/1952 | Dickey | 424/314 |
| 2,852,527 | 9/1958 | Steck | 260/482 R |
| 2,976,285 | 3/1961 | Gash | 260/471 A |
| 2,987,491 | 6/1961 | Bader | 260/482 R |
| 3,265,698 | 8/1966 | Allen et al. | 260/326.12 R |
| 3,420,827 | 1/1969 | Leffingwell | 260/482 R |

FOREIGN PATENTS OR APPLICATIONS

1,120,802 12/1961 Germany

OTHER PUBLICATIONS

Sonnet, J. Agr. Food Chem., 20(1), pp. 65–69, (1972).
Nilles, J. Agr. Food. Chem., 21(3), pp. 342–347, (1973).
Allen et al. II, J.A.C.S., 88, pp. 2536–2544, (1966).
Allen et al., Beilstein, vol. 4, p. 467, (1922).
Allen et al., Beilstein, 1st Supp., vol. 4, pp. 889–890, (1943).
Allen et al., Beilstein, 2nd Supp., vol. 4, pp. 1495–1496, (1963).
Arnold, Chem. Abst. 62:11672–3 (1965).
Krasnaya, Chem. Abst. 78:71347q (1973).
Wright, Chem. Abst., 81:22188s (1974).

*Primary Examiner*—Lorraine A. Weinberger
*Assistant Examiner*—Michael Shippen
*Attorney, Agent, or Firm*—Burgess, Dinklage & Sprung

[57] ABSTRACT

N-substituted β-aminocrotonic acid esters of the formula

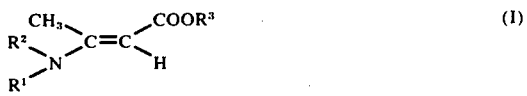

in which
R¹ is hydrogen, or alkyl or alkenyl with up to 4 carbon atoms;
R² is straight-chain or branched alkyl or alkenyl with up to 9 carbon atoms, optionally interrupted by O or S, and optionally substituted by halogen, phenoxy, dimethylamino, cyclic alkyl or alkenyl with up to 8 carbon atoms which are optionally substituted by halogen, dimethylamino, or alkyl, alkoxy or alkylthio with up to 4 carbon atoms, phenyl which is optionally substituted by halogen, dimethylamino, phenoxy, or alkyl, alkenyl, acyl, alkoxy, alkenoxy or alkynoxy containing up to 4 carbon atoms, or a 5- or 6-membered heterocyclic ring containing at least one O, S or N hetero-atom and optionally substituted by halogen, alkyl or alkoxy containing up to 4 carbon atoms or R₂ is further more cyclic alkyl or alkenyl with up to 8 carbon atoms optionally substituted by halogen, dimethylamino, or alkyl, alkoxy or alkylthio with up to 4 carbon atoms; phenyl optionally substituted by halogen, dimethylamino, phenoxy, or alkyl, alkenyl, acyl, alkoxy, alkenoxy or alkynoxy containing up to 4 carbon atoms; or a 5- or 6-membered heterocyclic ring containing at least one O, S or N heteroatom and optionally substituted by halogen, or alkyl or alkoxy containing up to 4 carbon atoms; or R¹ and R² together with the adjoining nitrogen atom form a heterocyclic structure optionally substituted by lower alkyl with 1–4 carbon atoms and optionally containing further heteroatoms in addition to nitrogen, and R³ is straight-chain or branched alkyl, alkenyl or alkynyl each with up to 10 carbon atoms, or cyclic alkyl or alkenyl with up to 8 carbon atoms, optionally substituted by halogen, alkoxy or alkyl-thio containing up to 4 carbon atoms, phenyl, 3,4-methylenedioxyphenyl, cyclic alkyl or alkenyl with up to 8 carbon atoms; phenyl optionally substituted by dioxymethylene or alkyl, alkenyl, alkynyl, alkoxy, alkenoxy, alkynoxy or acyl containing up to 4 carbon atoms; or a heterocyclic ring containing up to 6 atoms of which at least one is O, N or S, which ring is optionally bonded via alkyl containing up to 4 carbon atoms, which inhibit the metamorphosis of arthropods.

9 Claims, No Drawings

N-SUBSTITUTED β-AMINOCROTONIC ACID ESTERS

The present invention relates to and has for its objects the provision of particular new N-substituted β-aminocrotonic acid esters which inhibit the metamorphosis of arthropods, active compositions in the form of mixtures of such compounds with solid and liquid dispersible carrier vehicles, and methods for producing such compounds and for using such compounds in a new way especially for combating arthropods, e.g. insects and acarids, with other and further objects becoming apparent from a study of the within specification and accompanying examples.

The inhibition of metamorphosis to which this specification refers involves affecting the developmental metabolism of arthropods, by, for example, preventing the ecdysis of larvae, the transformation to the pupa or to the imago, the deposition of eggs capable of development, or the development of eggs which have been laid. This interrupts the generation cycle and reduces the population of the arthropods. This interference with development prevents the treated organisms from maturing and becoming capable of reproduction.

It is generally know that conventional animal biocides, for example phosphoric acid esters, when used as ingested poisons and contact poisons, kill both vertebrates and invertebrates through cholinesterase-inhibition. Furthermore, it is already known that, in contrast to these conventional biocides which act as contact poisons or ingested poisons and kill the animals in a few hours, a juvenile hormone, or substances chemically closely related to this hormone can be used to prevent the development of insects and spider mites, especially in the final phase of the development of pupae, or sexually mature imagos (J. J. Menn and M. Beroza: Insect Juvenilhormones, Chemistry & Action, Academie Press, New York 1972).

For this reason, a large number of investigations have concerned themselves with the chemical modification of the natural hormones. These investigations showed, in particular, that a fairly long unsaturated alkyl chain is responsible for good hormone activity (H. J. Zabik et al., J. Agr. Food Chem. 21, 342 (1973)).

Thus it has been found that β-aminocrotonic acid esters with citronellylamine or epoxycitronellylamine as the amino component are good juvenile hormone analogues (P. E. Sonnet et al., J. Agr. Food Chem. 20, 65 (1972)).

Further, it has been disclosed that β-aminocrotonic acid esters with long-chain amino groups and/or ester groups are good fungicides and acaricides (compare German Auslegeschrift (German Published Specification) 1,120,802).

However, it is a disadvantage of these compounds that the starting materials are too expensive, and that some of them can only be prepared with difficulty.

The present invention provides β-aminocrotonic acid esters of the general formula

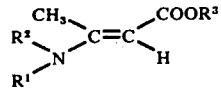   (I)

in which $R^1$ is hydrogen, or akyl or alkenyl with up to 4 carbon atoms;

$R^2$ is straight-chain or branched alkyl or alkenyl with up to 10 carbon atoms, optionally interrupted by O or S, and optionally substituted by halogen, phenoxy, dimethylamino, cyclic alkyl or alkenyl with up to 8 carbon atoms which are optionally substituted by halogen, dimethylamino, or alkyl, alkoxy or alkylthio with up to 4 carbon atoms, phenyl which is optionally substituted by halogen, dimethylamino, phenoxy, or alkyl, alkenyl, acyl, alkoxy, alkenoxy or alkynoxy containing up to 4 carbon atoms, or a 5- or 6-membered heterocyclic ring containing at least one O, S or N hetero-atom and optionally substituted by halogen, alkyl or alkoxy containing up to 4 carbon atoms or cyclic alkyl or alkenyl with up to 8 carbon atoms optionally substituted by halogen, dimethylamino, or alkyl, alkoxy or alkylthio with up to 4 carbon atoms; phenyl optionally substituted by halogen, dimethylamino, phenoxy, or alkyl, alkenyl, acyl, alkoxy, alkenoxy or alkynoxy containing up to 4 carbon atoms; or a 5- or 6-membered heterocyclic ring containing at least one O, S or N heteroatom and optionally substituted by halogen, or alkyl or alkoxy containing up to 4 carbon atoms; or $R^1$ and $R^2$ together with the adjoining nitrogen atom form a heterocyclic structure optionally substituted by lower alkyl with 1–4 carbon atoms and optionally containing further heteroatoms in addition to nitrogen, and $R^3$ is straight-chain or branched alkyl, alkenyl or alkynyl each with up to 10 carbon atoms, or cyclic alkyl or alkenyl with up to 8 carbon atoms, optionally substituted by halogen, alkoxy or alkyl-thio containing up to 4 carbon atoms, phenyl, 3,4-methylenedioxyphenyl, cyclic alkyl or alkenyl with up to 8 carbon atoms; phenyl optionally substituted by dioxymethylene or alkyl, alkenyl, alkynyl, alkoxy, alkenoxy, alkynoxy or acyl containing up to 4 carbon atoms; or a heterocyclic ring containing up to 6 atoms of which at least one is O, N or S, which ring is optionally bonded via alkyl containing up to 4 carbon atoms.

Preferably, $R^1$ is hydrogen, alkyl or alkenyl with up to 3 carbon atoms, especially methyl, ethyl or allyl; $R^2$ is straight-chain or branched alkyl with up to 9 carbon atoms which can optionally be substituted by norbornyl, morpholine, chlorine, phenoxy, cyclohexyloxy, cyclohexy, cyclohexenyl, methylcyclohexenyl, furfuryl or dimethylamine and can be interrupted one or more times by O or S, or $R^2$ is cyclopentyl, cyclohexyl, cycloheptyl or cyclooctyl which are optionally substituted by methyl, isopropyl, methoxy or ethoxy, or allyl, or phenyl which is optionally substituted by chlorine, bromine, methyl, ethyl, ethoxy, allyloxy, propargyloxy, dimethylamino, phenoxy or acetyl, or benzyl which is optionally substituted by chlorine or ethyl; or $R^1$ and $R^2$ and the adjoining nitrogen atom form an optionally methyl-substituted 5-, 6- or 7-membered heterocyclic structure which can additionally contain N or O as a further heteroatom, especially morpholine, piperazine, piperidine, pyrrolidine or azepine; and $R^3$ is straight-chain or branched alkyl with 1 – 10 carbon atoms, which can optionally be interrupted by O or S, lower alkenyl or alkynyl with up to 4 carbon atoms, phenyl, acetylphenyl, propargyloxyphenyl, ethylphenyl, ethylmercaptophenyl, isopropoxyphenyl, furfuryl, tetrahydrofurfuryl, 3,4-methylenedioxyphenyl or 3,4-methylenedioxybenzyl.

These compounds have been found to inhibit the development of arthropods, especially insects and spider mites, above all during the ecdysis stages. The mode of action of the active compounds according to the invention is novel and differs both from that of conventional insecticides and from that of chemosterilizing agents and of insect hormones.

It is distinctly surprising that the compounds according to the invention, of the formula (I), exhibit a metamorphosis-inhibiting action, especially since only a very short-chain amine suffices to produce the full action. It follows from this that in contrast to previously known investigations, the length of the alkyl chain is of subordinate importance, at least in the case of this particular system. Apparently, it is the β-substituted crotonic acid ester structure which is essential to produce a good action.

A particular advantage of the active compounds according to the invention is a pronounced genus-specific action. In this way it is possible to develop agents which are only active against certain pests. These active compounds are thus of particular importance in developing new methods, less detrimental to the environment, of combating pests.

The compounds according to the invention have the further advantage that they can be prepared simply and inexpensively.

The invention also provides a process for the production of a β-aminocrotonic acid ester according to the invention in which a. an acetoacetic acid ester of the general formula $$CH_3-CO-CH_2-COOR^3 \quad (II)$$

in which
R³ has the abovementioned meaning, is reacted with an amine of the general formula

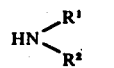 (III)

in which
R¹ and R² have the abovementioned meanings, optionally in the presence of an organic diluent, or b. an amine of the general formula (III) is reacted with a tetrolic acid ester of the general formula $$CH_3-C\equiv C-COOR^3 \quad (IV)$$

in which
R³ has the abovementioned meaning, optionally in the presence of a diluent, or c. an amine of the general formula (III) is reacted with β-chlorocrotonic acid ester of the general formula

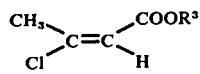 (V)

in which
R³ has the abovementioned meaning,
optionally in the presence of a diluent and of an acid-binding agent.

If allylamine and acetoacetic acid ethyl ester are used as starting materials, the course of the reaction of process variant (a) can be represented by the following equation:

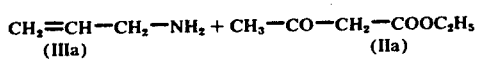

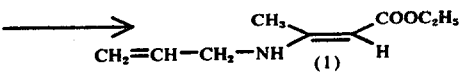

The reaction can be carried out according to the conditions indicated in J. Am. Chem. Soc., Volume 88 (1966) page 2,541. This process variant is preferred because of the ready availability of the starting compounds. Amines of the formula (III) and acetoacetic acid esters of the formula (II) used therein are known and can be prepared according to known processes.

Preferably, the amines indicated below are employed in carrying out the indicated process variants: ethylamine, propylamine, isopropylamine, butylamine, isobutylamine, tert.-butylamine, pentylamine, 2,2-dimethylpropylamine, pentyl(2)-amine, hexylamine, 2-ethylhexylamine, heptylamine, octylamine, dimethylamine, diethylamine, 2-chloroethylamine, 3-dimethylaminopropylamine, allylamine, 3-ethyl-pentene (3)-amine, diallylamine, 3-methoxypropylamine, 3-ethoxy-propylamine, 3-butoxy-propylamine, cyclohexylamine, 3-ethylhexylamine, 4-ethylhexylamine, 3-isopropylhexylamine, 4-isopropylhexylamine, hexamethyleneimine, 3-ethoxyhexylamine, 4-ethoxyhexylamine, 3-methylhexylamine, cyclopentylamine, 3-cyclohexoxypropylamine, octylamine, 4,7-dioxaoctylamine, 4,7-dioxanonylamine, 4,7,9-trioxadodecylamine, 4,7-dioxaundecylamine, 3-isopropoxypropylamine, 3-isobutoxypropylamine, 4-methoxypentylamine, 2(3-methylpentoxy)-ethylamine, 2-(cyclohexen(3)-yl)-ethylamine, 3-methylhexen(3)yl-methylamine, cyclohexen(3)yl-methylamine, 2-norbornylmethylamine, morpholine, furfurylamine, pyrrolidine, piperidine, N-methylpiperazine, N(3-aminopropyl)-morpholine, phenylamine, 4-chlorophenylamine, 4-bromophenylamine, 3-ethylphenylamine, 3-ethoxyphenylamine, 3-allyloxyphenylamine, 2-propargyloxyphenylamine, 4-dimethylaminophenylamine, 4-phenoxyphenylamine, 4-acetylphenylamine, benzylamine, 4-chlorobenzylamine, 4-ethylbenzylamine, 2-ethylthioethylamine and 2-phenoxyethylamine.

Preferably, the acetoacetic acid esters indicated below are used in carrying out the most important process variant (a): acetoacetic acid methyl ester, ethyl ester, propyl ester, isopropyl ester, butyl ester, i-butyl ester, t-butyl ester, pentyl ester, i-pentyl ester, hexyl ester, 1,3-dimethylbutyl ester, heptyl ester, octyl ester, allyl ester, propargyl ester, 2-chloroethyl ester, 2-isopropoxyethyl ester, cyclohexyl ester, benzyl ester, 4-acetyl-phenyl ester, 4-ethyl-phenyl ester, 3,4-methylenedioxyphenyl ester, furfuryl ester, tetrahydrofurfuryl ester, phenyl ester, p-chlorophenyl ester, o-isopropoxyphenyl ester, o-allyloxyphenyl ester, thiophenyl ester, 4-ethylthiophenyl ester, 3,4-methylenedioxybenzyl ester, cyclohexenyl ester, 2-ethylthioethyl ester, 2-cyclohexylethyl ester, o-propargyloxyphenyl ester or 4-allylphenyl ester.

If isobutylamine and tetrolic acid ethyl ester are used as starting materials, the course of the reaction in process variant (b) can be represented by the following equation:

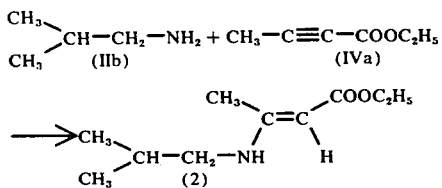

The reaction can be carried out analogously to the process indicated in Chemische Berichte, Volume 99, page 450.

If allylamine and β-chlorocrotonic acid ethyl ester are used as starting materials, the course of the reaction of process variant (c) can be represented by the following equation:

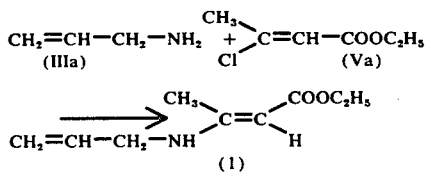

The invention of course encompasses both cis- and trans-isomers of the compounds of formula (I). In practice, the abovementioned process for the preparation of these compounds generally result in a predominant production of the trans-isomers.

If desired a diluent may be used in the processes indicated. All inert organic solvents can be used for this purpose. In the case of variant (a), a solvent together with which the water of reaction can be distilled off azeotropically, such as toluene or methylene chloride, is preferred.

In the case of process variant (c), an excess of amine is preferably employed as an acid-binding agent.

In other respects, the starting compounds are generally employed in molar amounts when carrying out the process variants according to the invention. An excess of one or other starting component is not detrimental but also produces no significant increase in the yield of compounds according to the invention.

The reaction temperatures can be varied over a substantial range; in general, the reaction is carried out at 0° to 100° C, preferably 20° to 50° C.

The following may be mentioned individually as new active compounds of formula (I): β-allylaminocrotonic acid 4-acetylphenyl ester, β-allylaminocrotonic acid 4-ethylphenyl ester, β-allylaminocrotonic acid 3,4-methylenedioxy-phenyl ester, β-furfurylaminocrotonic acid propyl ester, β-morpholinocrotonic acid propyl ester, β-allylaminocrotonic acid furfuryl ester, β-allylaminocrotonic acid tetrahydrofurfuryl ester, β-allylaminocrotonic acid 4-propargyloxyphenyl ester, β-allylaminocrotonic acid 4-ethylmercaptophenyl ester, β-allylaminocrotonic acid thiophenyl ester, β-allylaminocrotonic acid 3,4-methylenedioxybenzyl ester, β-allylaminocrotonic acid cyclohexyl ester, β-allylaminocrotonic acid benzyl ester, β-allylaminocrotonic acid o-isopropoxyphenyl ester, β-anilinocrotonic acid ethyl ester, β-diallylaminocrotonic acid ethyl ester, β-(2-chloroethyl)-aminocrotonic acid ethyl ester, β-pyrrolidinocrotonic acid ethyl ester, β-piperidinocrotonic acid ethyl ester, β-(N-methyl-piperazino)-crotonic acid ethyl ester, β-[N-(3-aminopropyl)-morpholino]-crotonic acid ethyl ester, β-(4-chloroanilino)-crotonic acid ethyl ester, β-(4-bromoanilino)-crotonic acid ethyl ester, β-(3-ethylphenylamino)-crotonic acid ethyl ester, β-(3-ethoxyphenylamino)-crotonic acid ethyl ester, β-(3-allyloxyphenylamino)-crotonic acid ethyl ester, β-(2-propargyloxyphenylamino)-crotonic acid ethyl ester, β-(4-dimethylaminophenylamino)-crotonic acid ethyl ester, β-(4-phenoxyphenylamino)-crotonic acid ethyl ester, β-(4-acetylphenylamino)-crotonic acid ethyl ester, β-benzylaminocrotonic acid ethyl ester, β-(4-chlorobenzylamino)-crotonic acid ethyl ester, β-(4-ethylbenzylamino)-crotonic acid ethyl ester, β-(2-ethylthioethylamino)-crotonic acid ethyl ester, β-(2-phenoxyethylamino)-crotonic acid ethyl ester, β-diethylamino-crotonic acid ethyl ester, β-dimethylaminocrotonic acid ethyl ester and β-allylaminocrotonic acid 2-ethyl-mercaptoethyl ester.

The active compounds according to the invention, which have a low toxicity to warm-blooded animals and low phytotoxicity, surprisingly exhibit a specific metamorphosis-inhibiting action. This action manifests itself during the ecdysis which is typical of arthropods only and in some cases the action also continues over several stages of development and first comes into play during the transformation to the chrysalis or during slipping. The active compounds can, therefore, be used very successfully for combating harmful arthropods, especially harmful sucking and biting insects and spider mites. They may, therefore, be used in plant protection and the protection of stored products, in the hygiene field and for destroying insects in permanently or temporarily stagnant waters. They furthermore have a degree of fungicidal and plant growth-regulating activity.

The arthropods include, for example, orders and species such as the Entomostraca, for example *Artemia salina;* the Cladocera, for example species of Daphnia, and the Copepoda, for example *Cyclops vernalis;* and the Malacostraca, amongst which are counted the Isopoda including *Oniscus asellus, Armadillidium vulgare* and the genus Gammaridae. The Diplopoda include species such as *Glomeris pustulata* and *Blaniulus guttulatus;* the Chilopoda, including Scutigera species, *Lithobius forficatus* and *Geophilus carpophagus;* and the Symphyla, including *Scutigerella immaculata.* The Arachnida include pests and venomous animals such as *Chelifer cancroides, Buthus occitanus, Latrodectus mactans* and the genus Mygale. The harmful Acarina include species such as *Dermanyssus gallinae* and plant pests such as *Eriophyes ribis, Phyllocoptruta oleivora, Tarsonemus pallidus, Panonychus citri* and ulmi, *Tetranychus urticae, Tetranychus telarius, Tetranychus tumidus* and the Ixodoidea such as Dermacentor species, and *Ornithodorus moubata.* The Hexpods include the Thysanura such as *Lepisma saccharina;* the Collembola such as Onychiurus species; the Plecoptera; the Orthoptera such as *Blatta orientalis, Periplaneta americana* and *Acheta domesticus,* and agricultural pests such as *Locusta migratoria, Melanoplus differentialis* and *Schistocera gregaria;* and the Dermaptera, for example *Forficula auricularia.* Also to be mentioned are the harmful insects of the Isoptera such as *Reticulitermes* species; the Mallophaga, such as Trichodectidae species; the Anoplura such as *Pediculus humanus corporis, Phylloxera vastatrix* and Pemphigus species; and the Thysanoptera such as *Hercinothrips femoralis* and *Thrips tabaci.* The harmful Heteroptera include, for example, *Cimex lectularius, Rhodnius prolixus, Triatoma infestans* and plant pests such as Eurygaster species, *Dysdercus intermedius* and *Piesma quadrata.*

Amongst the Homoptera are included species such as *Aleurodes brassicae, Bemisia tabaci, Dialeurodes citri, Aphis gossypii, Brevicoryne brassicae, Cryptomyzus ribis, Doralis fabae* and *pomi, Myzus persicae, Phorodon humuli* and *Rhopalosiphum padi*. The Cicadellidae include species such as Euscelis bilobatus, *Lecanium corni, Saissetia oleae, Laodelphax striatellus, Aonidiella aurantii*, Pseudococcus species and species of Psylla. The harmful Lepidoptera include species such as *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria species, Bucculatrix thurberiella, Phyllocnistis citrella, Agrotis* species, Euxoa species, Feltia species, *Earias insulana*, Heliothis species, *Laphygma exigua, Mamestra brassicae, Panolis flammae, Prodenia litura*, Spodoptera species, *Trichuplusia ni, Carpocapsa pomonella*, Pieris species, Chilo species, *Pyraustra nubilalis, Ephestia kuhniella, Galleria mellonella*, Capua reticulana, Choristoneura fumiferana, Clysia ambiguella and *Tortrix viridana*. The order of the Coleoptera includes domestic pests, pests of stored products and plant pests such as *Acanthoscelides obtectus, Oryzaephilus surinamensis, Dermestes peruvianus, Trogoderma granarium, Sitophilus granarius, Tribolium confusum*, Tenebrio species, *Leptinotarsus decemlineata, Phaedon cochleariae, Epilachna varivestis*, Anthomomus species, *Anthremus verbasci*, Diabrotica species, Agriotis species, and Melolontha vulgaris. Amongst the Hymenoptera are included organisms such as Diprion species and Haplocampa species. The Diptera include harmful species such as *Oscinella frit, Drosophila melanogaster, Pegomyia hyoscyami, Ceratitis capitata, Dacus oleae, Phorbia* species, *Calliphora erythrocephala, Aedes aegypti, Anopheles stephensi, Stomoxys calcitrans, Tabanus bovinus*, Phlebotomus species and the Simuliidae. The Siphonapetra include species such as *Xenopsylla cheopis*.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.) cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as nematocides, insecticides, acaricides, fungicides, bactericides, rodenticides, herbicides, fertilizers, growth-regulating agents, etc., if desired, or in the form of particular dosage preparations for specific application made therefrom, such as solutions, emulsions, suspensions, powders pastes, and granules which are thus ready for use.

Other known active compounds include dimethylcarbamates such as 5,5-dimethyl-4,5-dihydroresorcinol-dimethylcarbamate, 1-isopropyl-3-methyl-5-pyrazolyl-dimethylcarbamate, 1-phenyl-3-methyl-5-pyrazolyl-dimethylcarbamate, 2-dimethylcarbamyl-3-methyl-5-pyrazolyl-dimethylcarbamate, 1(2-alkoxycarbonylethyl)-3-methylpyrozalyl 5-dimethylcarbamate, 2-n-propyl-4-methyl-6-pyrimidyl-dimethylcarbamate, as well as methylcarbamates of phenols such as 3,4-dimethyl-6-chlorophenyl methylcarbamate, 3-methyl-5-isopropylphenyl methylcarbamate, 2-(1-methylpropyl)-phenyl methylcarbamate, m-tolyl N-methylcarbamate, 3,4,5-trimethylphenyl methylcarbamate, 2-chlorophenyl methylcarbamate, 3,4-dimethyl phenyl N-methylcarbamate, 3,5-di-tert.-butylphenyl methylcarbamate, 2-(1,3-dioxolan-2-yl)-phenyl methylcarbamate, 3-methyl-4-dimethylaminophenyl N-methylcarbamate, 3,5-dimethyl-4-diallylaminophenyl methylcarbamate, 3,5-dimethyl-4-dimethylaminophenyl methylcarbamate, 3(N,N-dimethylaminomethyleneimino)-phenyl-methylcarbamate, dimethylaminomethyleneimino)-phenyl-methylcarbamate, 2-isopropoxyphenyl methylcarbamate, 3,5-dimethyl-4-methylmercaptophenyl N-methylcarbamate, as well as carbamates of polynuclear compounds such as 1-naphthyl methylcarbamate, 2,2-dimethyl-2,3-dihydro-7-benzofuranyl methylcarbamate and 2-methyl-2,3-dihydro-7-benzofuranyl methylcarbamate, as well as methylcarbamates of oximes such as 1-methylthio-acetaldehyde-0-(methylcarbamoyl)-oxime and 2-methyl-2(methylthio)-propionaldehyde-0-(methylcarbamoyl)-oxime, and also phosphoric acid esters such as 4',4'-bis-(0,0-dimethylthionophosphoryloxphenyl)-sulfide, 0-ethyl-0-

(2,4,5-trichlorophenyl)-ethanethiophosphonic acid ester, 0,0-dimethyl-0-[4(4'-chlorophenylazo)-phenyl]-thiophosphoric acid ester, 0,0-diethyl-0-(3-chloro-4-methyl-7-coumarinyl)-thiophosphoric acid ester, 0,0-diethyl-0-[quinoxalyl(2)]-thionophosphoric acid ester, 0,0-dimethyl-0-(3-chloro-4-nitrophenyl)-thionophosphoric acid ester, S-(0,0-dimethylthionophosphoryl)-1-. phenyl-1-mercaptoacetic acid ethyl ester, 0,0-dimethyl-(1-hydroxy-2,2,2-trichloroethyl)-phosphonic acid ester, 0,0-diethyl-S-(2-ethylmercaptoethyl)-dithiophosphoric acid ester, 0,0-diethyl-S-(ethylsulfinylethyl)-dithiophosphoric acid ester, 0,0-diethyl-0-[3,5,6-trichloropyridyl-(2)]-thiophosphoric acid ester, 0,0-dimethyl-S-(methylcarbamoylmethyl)-thiophosphoric acid ester, 0,0-dimethyl-0-(3-methyl-4-nitrophenyl)-thiophosphoric acid ester, 0,0-dimethyl-S-(4-oxobenzotriazine-3-methyl)-dithiophosphoric acid ester, 0-ethyl-S,S-diphenyldithiophosphoric acid ester, 0,0-dimethyl-S-phthalimidomethyl-dithiophosphoric acid ester, 0,0-dimethyl-S-(p-chlorophenylmercaptomethyl)-dithiophosphoric acid ester, 0,0-dimethyl-0-(2-ethylmercaptoethyl)-thiolphosphoric acid ester, 0,0-diethyl-S-benzyl-thiolphosphoric acid ester, 0-phenyl-N,N'-dimethylphosphoric acid diamide, 0,0,0',0'-tetraethyl-S,S'-methylene-bis-dithiophosphoric acid ester, tetra-n-propyldiethionopyrophosphoric acid ester, 0,0-diethyl-0-[3-methylpyrazolyl(5)]-phosphoric acid ester, 0,0-dimethyl-S-(N-methylcarbamoylmethyl)-dithiophosphoric acid ester, 2-methoxy-4-H-1,3,2-benzodioxaphosphorane-2-thione, 0,0-dimethyl-S-[5-methoxy-1,3,4-thiadiazol-2-(3-H)-on-3-yl-methyl]-dithiophosphoric acid ester, 0,0-diethyl-0-(p-methyl sulfinylphenyl)-thiophosphoric acid ester, 0,0-diethyl-S-(ethylmercaptomethyl)-dithiophosphoric acid ester, 0,0-dimethyl-S-[2-(1-methylcarbamoylethylmercapto)-ethyl]-dithiophosphoric acid ester, 0-methyl-0-(2,4-dichlorophenyl)-N-isopropylthiophosphoric acid amide, and also the naturally occurring pyrethrins such as chrysanthemum-acid, pyrethric acid and pyrethroids such as Pyrethrum, Allethrin, Cyclethrin, Barthrin, Dimethrin, Phthalthrin and Japothrin, and also rotenoids, as well as alkaloids, insecticidal proteins such as microbial insecticides, fluoroacetic acid derivatives, thiocyanic acid esters, such as $\beta$-butoxyethoxyethyl thiocyanate, diarylmethanes and diarylcarbinols such as 1,1-bis-(4chlorophenyl)-2,2,2-trichloroethane and 1,1-bis-(4-chlorophenyl)-ethanol, nitrophenol derivatives such as 4,6-dinitro-2-cyclohexylphenol, 4,6-dinitro-2-cyclohexylphenol dicyclohexylamine salt, 4-nitro-2,6-di-tert.-butylphenol and 4,6-dinitro-2-(1-methylheptyl)-phenylcrotonate, diaryl thioethers and diarylsulfones, such as 2,4,5,4'-tetrachlorodiphenylsulfide, diphenylsulfone, aryl-benzyl-thioethers, -sulfoxides and -sulfones and aryl-alkyl-thioethers, diaryloxy- and diarylmercapto-alkanes, arylhydrazine compounds and arylazo compounds, such as azobenzene, and amidines, such as N-(2-methyl-4-chlorophenyl)-N',N'-dimethylformamidine.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of inhibiting metamorphosis of arthropods which comprises applying to at least one of correspondingly (a) such arthropods and (b) the corresponding habitat thereof, i.e. the locus to be protected, e.g. to a growing crop, to an area where a crop is to be grown or to a domestic animal, a correspondingly inhibitory amount of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples.

The experiments described in Examples 1 to 3 illustrate the arthropod metamorphosis-inhibiting action of compounds according to the invention, without implying any restriction with regard to the breadth of action of these compounds. In these experiments the morphological changes, such as half-formed pupae, incompletely slipped larvae or caterpillars, defective wings, pupal cuticula in the case of imagos, and mortality, are assessed over the entire specified development of the test animals. The sum of the morphological malformations and mortality during development is quoted as a value index, and the indexes have the following meanings.

1 = 90 – 100% malformation or mortality
2 = 80 – 89% malformation or mortality
3 = 70 – 79% malformation or mortality 4 = 60 – 69% malformation or mortality
5 = 50 – 59% malformation or mortality
6 = 40 – 49% malformation or mortality
7 = 30 – 39% malformation or mortality
8 = 10 – 29% malformation or mortality
9 = 0 – 9% malformation or mortality

EXAMPLE 1

Metamorphosis-inhibiting action/ingestion test

Test insects: *Plutella maculipennis* (caterpillars in the 4th stage of development) — 20 specimens *Phaedon cochleariae* (larvae) — 20 specimens Feed plants: Cabbage plants (*Brassica oleracea*)
Solvent: 10 parts by weight of acetone
Emulsifier: 1 part by weight of polyoxyethylene sorbitan monolaurate To produce a suitable preparation of active compound, 2 parts by weight of active compound were mixed with the stated amount of solvent and emulsifier and sufficient water to produce a 1% strength mixture which was diluted with water to the desired concentration.

The test insects were fed with leaves of the feed plants, which carried a uniform sprayed coating of the active compound mixture of the stated concentration, until the imago developed.

As a control, specimens were fed with leaves which had only been treated with solvent and emulsifier of the stated concentrations. The results can be seen from the table which follows:

Table 1

Metamorphosis-inhibiting action/ingestion test

| Test insects: Active compound concentration: | Phaedon 0.01% | Plutella 0.01% | 0.001% |
|---|---|---|---|
| Control | 9 | 9 | 9 |
| Active Compound No. $CH_2=CH-CH_2-$ (1) | 5 | 1 | 1 |
| (2) | 8 | 2 | 2 |
| (5) | 6 | 2 | 2 |
| (6) | 5 | 2 | 2 |
| (7) | 8 | 1 | 1 |
| (8) | 6 | 1 | 1 |
| (9) | 8 | 1 | 1 |
| (10) | 6 | 1 | 1 |

EXAMPLE 2

Metamorphosis-inhibiting action/Laphygma test

Test insects: *Laphygma exigua* (caterpillars)

Feed: 1 cm thick disc, of 3 cm diameter, of partially air-dried synthetic feed of shredded beans, yeast, vitamin mixture, powdered leaf, agar and preservative Solvent: 10 parts by weight of acetone
Emulsifier: 1 part by weight of polyoxyethylene-(20) sorbitan monolaurate To produce a suitable preparation of active compound, 2 parts by weight of active compound were mixed with the stated amount of solvent and emulsifier and sufficient water to give a 1% strength mixture which was diluted with water to the desired concentration.

One test insect per disc was placed on a feed disc which had been moistened with 1.5 ml of active compound solution of the stated concentration and was observed until the imago slipped.

As a control, one test insect per disc was placed on a feed disc moistened with 1.5 ml of solvent and emulsifier of the correspondng concentration and observed until the imago slipped. The results can be seen from the table which follows:

Table 2

| Metamorphosis-inhibiting action/Laphygma test Test insects: Active compound concentration | Laphygma 0.1% | 0.001% |
|---|---|---|
| Control | 9 | 9 |
| Active Compound No. (1) | 1 | 4 |
| (5) | 2 | 2 |
| (7) | 2 | 6 |
| (8) | 2 | 4 |
| (9) | 1 | 1 |
| (10) | 1 | 2 |

EXAMPLE 3

Metamorphosis-inhibiting action/*Aedes aegypti* test

Test insects: *Aedes aegypti* (larvae)
Solvent: 10 parts by weight of acetone
Emulsifier: 1 part by weight of polyoxyethylene-(20) sorbitan monolaurate To produce a suitable preparation of active compound, 2 parts by weight of active compound were mixed with the stated amount of solvent and emulsifier and sufficient water to produce a mixture containing 100 ppm, which was diluted with water to the desired concentration.

The test insects were dipped in 90 ml of these active compound solutions and observed until the imago slipped. As a control, test insects were introduced into a mixture of solvent, emulsifier and water of the stated concentration and observed until the imago slipped.

The results can be seen from the table which follows:

Table 4

| Metamorphosis-inhibiting action/*Aedes aegypti* test | | |
|---|---|---|
| Test insects: | \multicolumn{2}{c}{*Aedes aegypti*} |
| Active compound concentration | 1 ppm | 0.1 ppm |
| Control | 9 | 9 |
| Active Compound No. | | |
| (4) 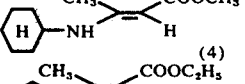 | 5 | 6 |
| (9) 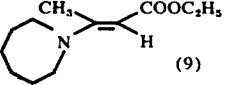 | 1 | 1 |
| (10) 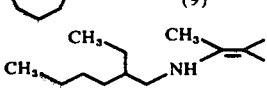 | 1 | 1 |

EXAMPLE 4

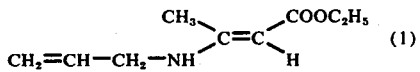 (1)

20.1 g (0.35 mole) of allylamine were added dropwise to 52 g (0.4 mole) of acetoacetic acid ethyl ester while stirring and cooling. The temperature was not permitted to exceed 45° C. The reaction mixture was then stirred for a further 4 hours at 45° C and subjected to vacuum distillation. Boiling point $_{18}$ = 125°–127° C, yield: 41 g (70% of theory).

The following were prepared analogously:

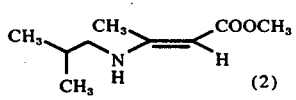 (2)    boiling point $_{0.15}$ = 67° C

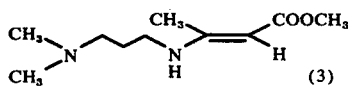 (3)    boiling point $_{0.7}$ = 124° C

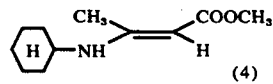 (4)    boiling point $_{0.3}$ = 115–117° C

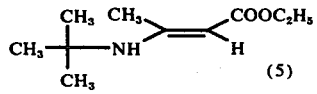 (5)    boiling point $_{16}$ = 120° C

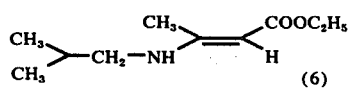 (6)    boiling point $_{18}$ = 120–130° C

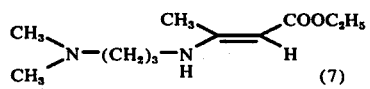 (7)    boiling point $_{0.15}$ = 125–127° C

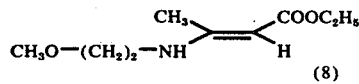 (8)    boiling point $_{0.2}$ = 120° C

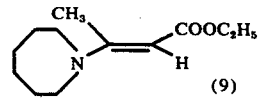 (9)    boiling point $_{0.6}$ = 151° C

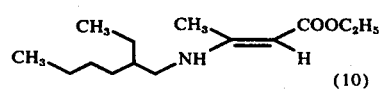 (10)    boiling point $_{0.7}$ = 130° C

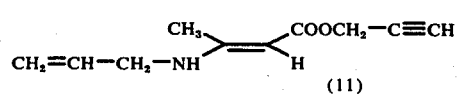 (11)    boiling point $_{15}$ = 100° C

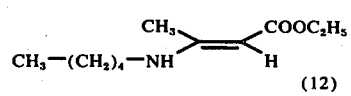 (12)    boiling point $_{0.25}$ = 80° C

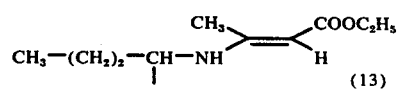 (13)    boiling point $_{0.25}$ = 70–72° C

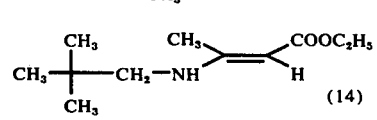 (14)    boiling point $_{0.2}$ = 72° C

-continued

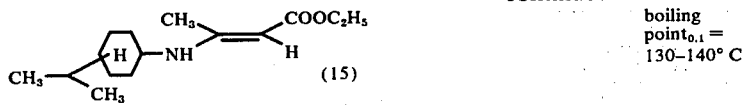 (15) boiling point$_{0.1}$ = 130–140° C

Mixture of 3,4-isopropyl compounds

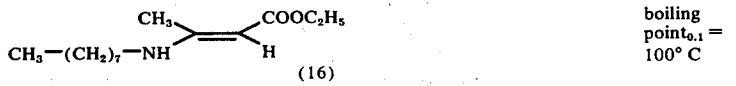 (16) boiling point$_{0.1}$ = 100° C

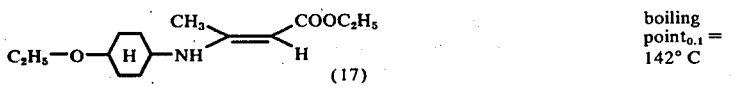 (17) boiling point$_{0.1}$ = 142° C

 (18) boiling point$_{0.1}$ = 104° C

 (19) boiling point$_{0.1}$ = 110–115° C

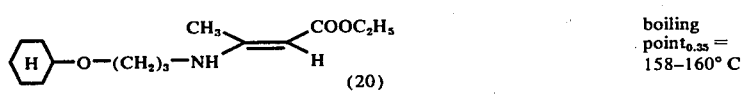 (20) boiling point$_{0.35}$ = 158–160° C

 (21) boiling point$_{0.1}$ = 120–122° C

 (22) boiling point$_{0.2}$ = 140–145° C

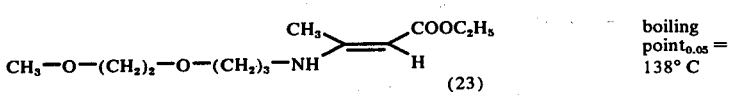 (23) boiling point$_{0.05}$ = 138° C

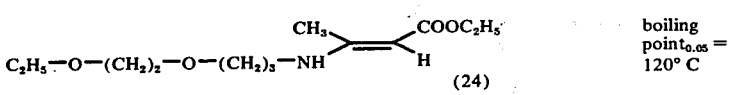 (24) boiling point$_{0.05}$ = 120° C

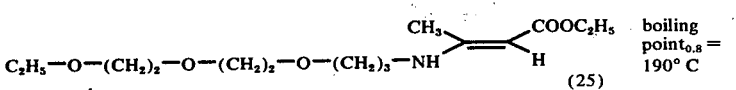 (25) boiling point$_{0.8}$ = 190° C

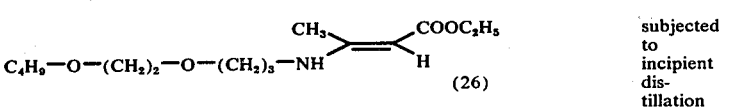 (26) subjected to incipient distillation

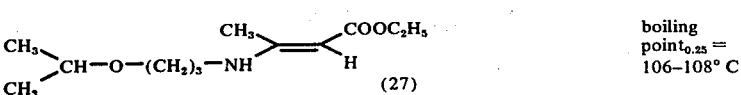 (27) boiling point$_{0.25}$ = 106–108° C

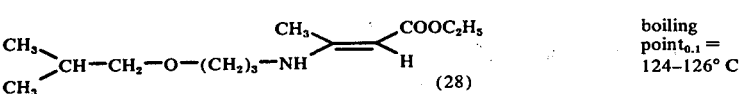 (28) boiling point$_{0.1}$ = 124–126° C

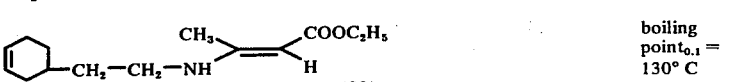 (29) boiling point$_{0.1}$ = 130° C

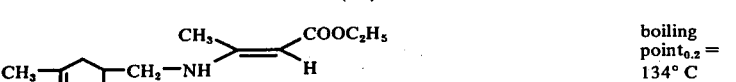 (30) boiling point$_{0.2}$ = 134° C

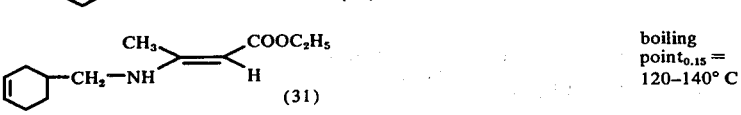 (31) boiling point$_{0.15}$ = 120–140° C

-continued

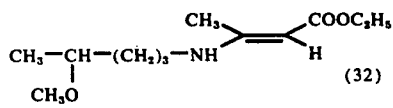 (32) boiling point$_{0.2}$ = 110–115° C

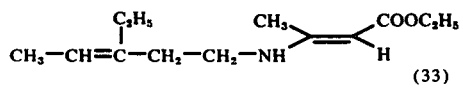 (33) boiling point$_{0.2}$ = 116–118° C

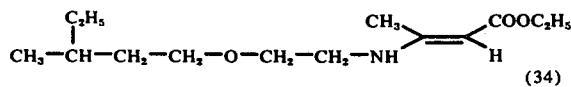 (34) boiling point$_{0.2}$ = 134–138° C

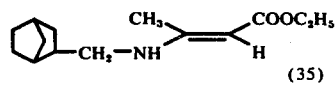 (35) boiling point$_{0.1}$ = 130–135° C

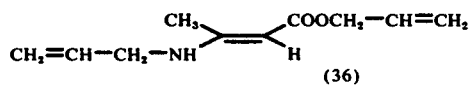 (36) boiling point$_{0.1}$ = 99–102° C

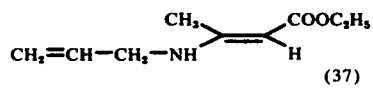 (37) boiling point$_{0.1}$ = 124–127° C

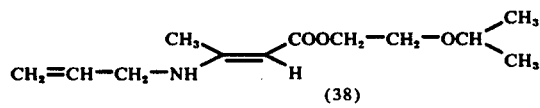 (38) boiling point$_{0.1}$ = 100–104° C

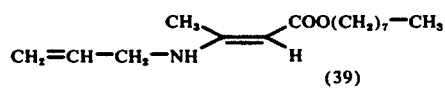 (39) boiling point$_{0.2}$ = 130–134° C

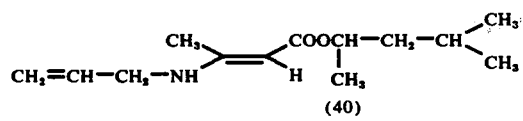 (40) boiling point$_{0.15}$ = 95–97° C

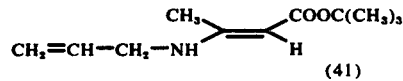 (41) boiling point$_{0.3}$ = 75–80° C

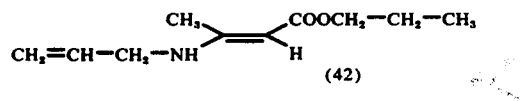 (42) boiling point$_{0.2}$ = 91–94° C

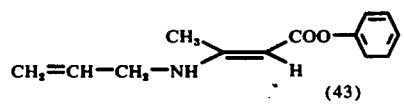 (43) melting point 50° C

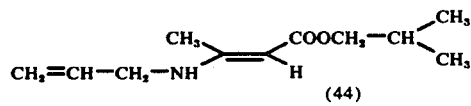 (44) boiling point$_{0.15}$ = 100–105° C

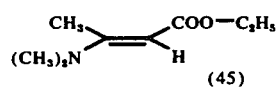 (45) boiling point$_{40}$ = 160–165° C

EXAMPLE 5

The illustrated compound

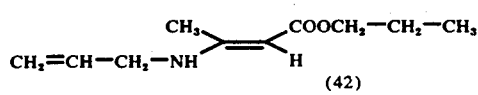 (42)

was also prepared as follows:

16.3 g of β-chlorocrotonic acid propyl ester were dissolved in 100 ml of toluene. 10.3 g of allylamine were then slowly added dropwise. The mixture was then stirred for a further 2 hours at 40° C and the hydrochloride which had precipitated was filtered off. The filtrate was subjected to distillation. The desired compound was obtained at boiling point$_{0.3}$ = 95°–100° C.

Other compounds which can be similarly prepared include:

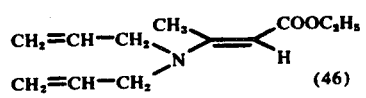
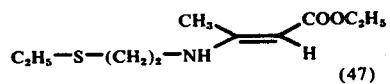
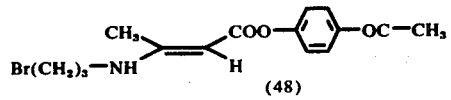
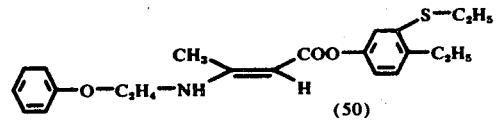
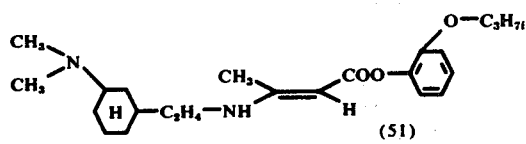
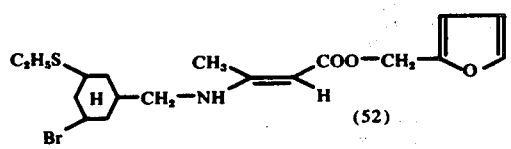
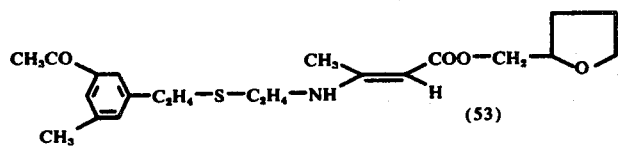
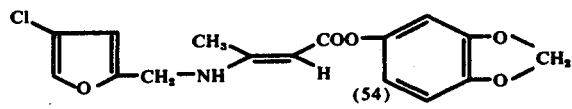
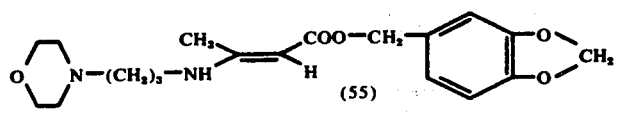
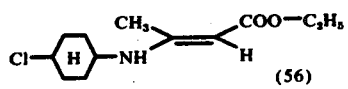
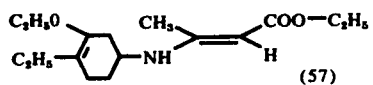
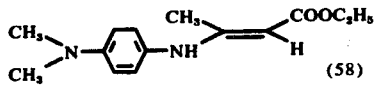
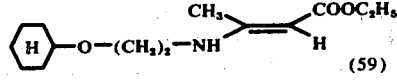
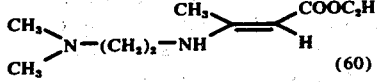
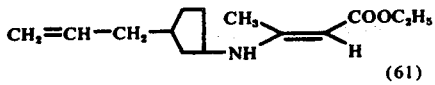

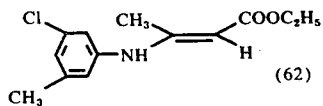
(62)

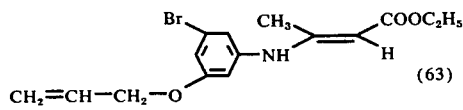
(63)

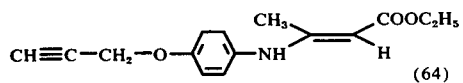
(64)

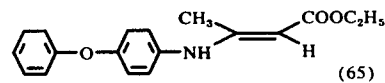
(65)

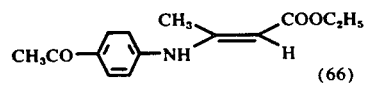
(66)

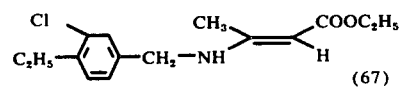
(67)

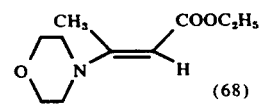
(68)

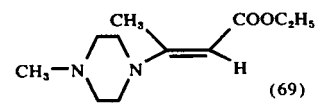
(69)

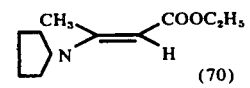
(70)

It will be appreciated that the instant specification and examples are set forth by way of illustration and not limitation, and that various modifications and changes may be made without departing from the spirit and scope of the present invention.

What is claimed is:

1. A compound selected from the group consisting of β-allylaminocrotonic acid ethyl ester of the formula

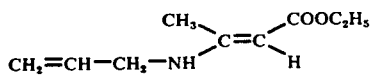

and β-(2-methoxyethylamino)-crotonic acid ethyl ester of the formula

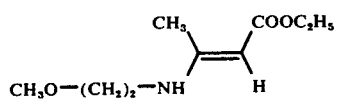

2. A compound according to claim 1 wherein such compound is β-allylaminocrotonic acid ethyl ester of the formula

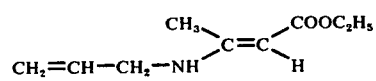

3. A compound according to claim 1 wherein such compound is β-(2-methoxyethylamino)-crotonic acid ethyl ester of the formula

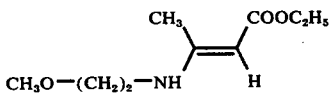

4. An arthropod metamorphosis inhibiting composition containing as active ingredient a metamorphosis inhibitory amount of a compound according to claim 1 in admixture with a diluent.

5. A method for combating arthropod pests which comprises applying to the pests or a habitat thereof a metamorphosis inhibitory amount of a compound selected from the group consisting of β-allylaminocrotonic acid ethyl ester, β-(2-methoxyethylamino)-crotonic acid ethyl ester, β-(2-ethylhexylamino)-crotonic acid ethyl ester, or β-(tert.-butylamino)-crotonic acid ethyl ester.

6. The method according to claim 5 wherein such compound is β-allylaminocrotonic acid ethyl ester.

7. The method according to claim 5 wherein such compound is β-(2-methoxyethylamino)-crotonic acid ethyl ester.

8. The method according to claim 5 wherein such compound is β-(2-ethylhexylamino)-crotonic acid ethyl ester.

9. The method according to claim 5 wherein such compound is β-(tert.-butylamino)-crotonic acid ethyl ester.

* * * * *

UNITED STATES PATENT AND TRADEMARK OFFICE
CERTIFICATE OF CORRECTION

PATENT NO. : 4,027,037
DATED : May 31, 1977
INVENTOR(S) : Peter Siegle, et al.

It is certified that error appears in the above-identified patent and that said Letters Patent are hereby corrected as shown below:

| | |
|---|---|
| Col. 2, line 48 | cancel "cyclohexy" and substitute -- cyclohexyl -- |
| Col. 5, line 2 | cancel "(IIb)" and substitute -- (IIIb) -- |
| Col. 6, line 42 | cancel "carpophagus" and substitute -- carpaophagus -- |
| Col. 7, line 19 | cancel "Kuhniella" and substitute -- Kühniella -- |
| Col. 8, line 34 | after "powders" insert -- , -- |
| Col. 8, line 42 | cancel "pyrozalyl" and substitute -- pyrazolyl -- |
| Col. 8, lines 56-57 | delete "dimethyl...carbamate" |
| Col. 8, line 68 | cancel "phosphoryloxphenyl" and substitute -- -- phosphoryloxyphenyl -- |
| Col. 9, line 26 | cancel "diethiono..." and substitute -- dithiono... -- |
| Col. 9, line 46 | cancel "(4chlorophenyl)" and substitute -- (4-chlorophenyl) -- |

UNITED STATES PATENT AND TRADEMARK OFFICE
CERTIFICATE OF CORRECTION

PATENT NO. : 4,027,037
DATED : May 31, 1977
INVENTOR(S) : Peter Siegle, et al.

It is certified that error appears in the above-identified patent and that said Letters Patent are hereby corrected as shown below:

Col. 11, line 35   drop "$CH_2=CH-CH_2-$" to join " $-NH$ " so as to read -- $CH_2=CH-CH_2-NH$ --

Signed and Sealed this thirtieth Day of August 1977

[SEAL]

Attest:

RUTH C. MASON
*Attesting Officer*

C. MARSHALL DANN
*Commissioner of Patents and Trademarks*